United States Patent
Pugia et al.

(10) Patent No.: US 8,304,254 B2
(45) Date of Patent: Nov. 6, 2012

(54) PIEZO DISPENSING OF A DIAGNOSTIC LIQUID ONTO A REAGENT SURFACE

(75) Inventors: Michael J. Pugia, Granger, IN (US); James A. Profitt, Goshen, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 227 days.

(21) Appl. No.: 12/598,150

(22) PCT Filed: Mar. 14, 2008

(86) PCT No.: PCT/US2008/056995
§ 371 (c)(1),
(2), (4) Date: Oct. 29, 2009

(87) PCT Pub. No.: WO2008/137213
PCT Pub. Date: Nov. 13, 2008

(65) Prior Publication Data
US 2010/0255592 A1  Oct. 7, 2010

Related U.S. Application Data

(60) Provisional application No. 60/915,519, filed on May 2, 2007.

(51) Int. Cl.
*G01N 1/38* (2006.01)
(52) U.S. Cl. .............. 436/180; 436/63; 436/66; 436/86; 436/95; 436/174; 222/1
(58) Field of Classification Search ............ 436/63, 436/66, 86, 88, 95, 164, 169, 174, 179, 180; 422/400, 420, 501, 515; 222/1
See application file for complete search history.

(56) References Cited

U.S. PATENT DOCUMENTS

| | | | |
|---|---|---|---|
| 3,814,668 A | 6/1974 | Blake et al. | |
| 3,843,053 A * | 10/1974 | Thoden | 239/11 |
| 4,849,340 A | 7/1989 | Oberhardt | |
| 4,879,097 A | 11/1989 | Whitehead et al. | |
| 5,063,396 A | 11/1991 | Shiokawa et al. | |
| 5,209,904 A | 5/1993 | Forney et al. | |
| 5,318,894 A | 6/1994 | Pugia | |
| 5,424,215 A | 6/1995 | Albarella et al. | |
| 5,518,179 A | 5/1996 | Humberstone et al. | |
| 6,083,763 A | 7/2000 | Balch | |
| 6,355,487 B2 | 3/2002 | Kowallis | |
| 6,394,363 B1 | 5/2002 | Arnott et al. | |
| 6,485,918 B1 | 11/2002 | Schermer et al. | |
| 6,656,432 B1 | 12/2003 | Hirota et al. | |
| 6,833,111 B2 | 12/2004 | Robertson et al. | |
| 2002/0041829 A1 | 4/2002 | Kowallis | |
| 2004/0043421 A1 | 3/2004 | Beumer et al. | |
| 2005/0084981 A1 | 4/2005 | Ostrowski et al. | |
| 2005/0287586 A1 * | 12/2005 | Bass | 435/6 |
| 2006/0263902 A1 | 11/2006 | Pugia et al. | |
| 2007/0199642 A1 * | 8/2007 | Natarajan | 156/89.11 |

FOREIGN PATENT DOCUMENTS

| | | |
|---|---|---|
| EP | 0353591 A2 | 2/1990 |
| EP | 1004870 A1 | 5/2000 |
| EP | 1094119 | 4/2001 |
| JP | 2001186880 | 7/2001 |
| JP | 2002542490 | 12/2002 |
| JP | 2005208037 | 8/2005 |
| JP | 2008542715 | 11/2008 |
| WO | 9222800 A1 | 12/1992 |
| WO | 0035590 A1 | 6/2000 |
| WO | 03072258 A1 | 9/2003 |
| WO | 2006127631 A1 | 11/2003 |
| WO | 2005033713 A1 | 4/2005 |
| WO | 2005061112 A1 | 7/2005 |
| WO | 2006043181 A2 | 4/2006 |

OTHER PUBLICATIONS

PCT/US2008/056995; PCT International Search Report and Written Opinion dated Jul. 4, 2008.
Notification of Reasons for Rejection of corresponding Japanese Patent Application No. 2010-506359 issued on Aug. 28, 2012.

* cited by examiner

*Primary Examiner* — Maureen Wallenhorst
(74) *Attorney, Agent, or Firm* — Noam R. Pollack

(57) ABSTRACT

Assays in which samples of biological fluids are dispensed onto reagent-containing porous substrates are improved in the accuracy and repeatability by dispensing the biological fluids in two or more fractions thereof, separated by intervals in which the biological fluid is not dispensed. Reagents and other fluids may be dispensed during the intervals when the biological fluid is not dispensed. Alternatively, reagents and other fluids may be dispensed in a similar manner onto substrates already containing biological fluids.

18 Claims, No Drawings

PIEZO DISPENSING OF A DIAGNOSTIC LIQUID ONTO A REAGENT SURFACE

FIELD OF THE INVENTION

This invention relates to reagents and instruments used to measure the quantity of analytes in biological samples by the reaction of the analytes with reagents to produce a detectable response.

BACKGROUND OF THE INVENTION

Depositing Liquids on Reagent-Containing Substrates

Many instruments have been developed to measure the quantity of analytes in biological samples, for example urine, blood, salvia, or extracts of mucus or tissue. Typically, a sample liquid is applied to a surface containing reagents that react with the analyte. The reagents produce a detectable response that is measured and related to the amount of the analyte. The surface usually will be either hydrophilic or hydrophobic in nature, e.g. filter paper compared to polystyrene. Some devices use combinations of surfaces, such as urinalysis strip tests that use hydrophilic filter paper pads on top of a hydrophobic polystyrene handle. In the typical test, a strip containing unreacted reagents is dipped, i.e. fully immersed in a liquid sample, and the reaction between the analyte in the sample and the reagents is measured, usually by optical methods. The unreacted reagents themselves may be water soluble or insoluble. They are deposited or immobilized and dried in a porous substrate. The substrate is attached or placed onto a supporting surface. Additionally, a liquid with or without reagents can be used during an assay. The liquid reagents can be applied to the surfaces of substrates already containing dried reagents, before, after or during the reaction with the analyte, typically being added after a sample has been applied. The volume of samples and reagents should be as small as possible for obvious reasons relating to cost and convenience. What is less obvious is that it is often difficult to obtain a uniform and accurate response when applying small amounts of liquid reagents or biological samples to surfaces containing reagents. The response of the analyte with reagents is reduced when the reaction area is smaller and when less analyte is present.

The substrate can be used to amplify the reaction response. Thin films, e.g. membranes, can be immobilized with affinity reagents to allow capturing and concentration of reactants in read zones. Directing flow of liquids in a desired direction, e.g. laterally rather than vertically, can increase efficiency by increasing the number of fluidic exchanges between the liquid sample or reagent and the reaction zone. Each exchange allows further reaction of the analyte to occur, thereby amplifying the signal. Modification of the surface of the substrate allows reagents to be isolated in the reaction zone. Further, the nature of the surface itself can be used to increase the reactivity of the analyte, for example by increasing solubilization of reagents or to favor reactions with reagents on the surface.

Most biological samples and liquid reagents will have a significant water content and thus will be compatible with hydrophilic substrates and incompatible with hydrophobic surfaces. The sample and reagent liquids when dispensed spread rapidly across hydrophilic substrates and are repelled by hydrophobic substrates. The contact between the dispensed liquid and the reagents on the surface is made by direct dispensing onto the reacted or partially reacted area. However, when substrates are relatively hydrophobic, the dispensed liquid will form beads on the surface of the substrate that attempt to minimize their contact with the surface and therefore they do not spread uniformly over the reagent. Another difficulty associated with dispensing liquids is that the dried reagents may be either water soluble or water insoluble in nature. The insoluble dry reagents may not be readily accessible to the liquid samples, or soluble reagents may be dissolved and move with the liquid on the substrate. The reagents ideally should contact the sample uniformly, since the measurable response of the reagents to the sample, e.g. color development, should be uniform in order to obtain an accurate reading of the quantity of the analyte in the sample.

Another problem related to obtaining good contact between a dispensed liquid and a reagent on a surface is related to the physical nature of the samples. They vary in their physical properties such as surface tension, viscosity, total solids content, particle size and adhesion. Therefore, they are not easily deposited in consistent volumes uniformly over the reagent-covered substrate. Also, as the amount of the liquid sample is reduced, it becomes increasingly difficult to apply a consistent amount of a sample having varying properties to the reagents. In contrast, ink jet printing and the like rely on liquids developed for such uses and having consistent physical properties.

Deposition of droplets of liquid is a familiar operation. Examples include the ink jet-printer, either piezoelectric or bubble actuated, which forms print from the controlled deposition of multiple small droplets of about 2 to 300 μm diameter (typically 50 μm) containing from a few femtoliters to tens of nanoliters. Other methods of depositing small droplets have been proposed, which generally employ piezoelectric principles to create droplets, although they differ from typical ink jet printers. Examples are found in U.S. Pat. Nos. 5,063,396; 5,518,179; 6,394,363; and 6,656,432. Deposition of larger droplets (3-100 μL) through a syringe type pipette is known to be reproducible in diagnostic systems. Such pipettes produce single droplet diameters of about 2 to 6 mm. A commercial example of such pipette systems is the CLINITEK ALTAS® urinalysis analyzer. The droplet size can be greater or less than the nozzle size depending on the nozzle shape, pump type and pressures applied.

The problems discussed above are particularly observed when a liquid sample is dispensed as droplets onto a reagent-containing pad. It has been found that the interactions of the pad's surface and the reagents were creating inaccurate responses when the sample was added as a droplet, rather than completely covering the reagent pad by immersing the reagent pad (dipping it) into the sample liquid. Large droplets on the order of 3 to 100 μL do not transfer into the reagent when the substrate is too hydrophobic and form a bubble on the surface. They overwhelm the reagent with excess fluid if the surface is hydrophilic. Smaller droplets, of a few femtoliters to tens of nanoliters, can also be a problem when deposited on a substrate that is too hydrophobic as they lack the volume to completely cover the surface area and will randomly aggregate in non-uniform patterns. Small drops also allow open spaces for migration of water-soluble reagents. These tiny droplets are also prone to evaporation of liquids and to formation of aerosols, which are considered to be biohazardous if comprised of urine or blood specimens. Thus, if a liquid is to be deposited as droplets on test pads, rather than dipping the pads in the sample, improvements have been needed.

After contact between dispensed liquids and reagents is complete, the results may be read using one of several methods. Optical methods are commonly used, which rely on spectroscopic images to produce responses. Results must be reproducible to be useful. Optical measurements are affected by the reagent area viewed and by the time allowed for the dispensed liquids and reagents to react. Formation of non-uniform areas within the field of view and changes in the amount of reaction time cause increased errors. For example, a measurement made of a sample or reagent which has spread non-uniformly across the substrate gives a different result each time it is read.

In co-pending U.S. patent application Ser. No. 11/135,928, published as U.S. 2006/0263902 A1, commonly assigned with this application, the inventors reported their methods of depositing biological fluids and reagents as fine droplets onto reagent-carrying substrates. They demonstrated that the reagent-carrying substrates behaved differently, depending on the water solubility of the reagents and the surface energy of the substrate, that is, whether the reagent-carrying substrates were hydrophilic or hydrophobic. Depositing large droplets, e.g. 1.7-20.4 μL, was shown to provide less accurate results than when small droplets of about 50 pL to 1 μL were deposited on reagent-carrying surfaces. The inventors also found that small droplets were absorbed by the hydrophobic substrates, while large droplets were not readily absorbed.

Water soluble reagents were shown to dissolve and move with a liquid as it spreads on a reagent-carrying surface. The inventors found that the non-uniform reagent response which such movement caused could be moderated by depositing small droplets.

Depositing of small droplets was done either by nozzles having many small openings or by single nozzles, which could be moved relative to the reagent-carrying substrate, or vice versa, to cover the desired area. The reaction of liquid samples with reagents on the substrate could be read as an average of the area covered by the sample or preferably by scanning the reaction area one spot at a time and averaging the results.

During further development of the methods described in published application 2006/0263902 A1, some problems were discovered, which resulted in the improved methods to be described below.

It has been found that, even after the problems just discussed have been overcome by proper design of the dispensing device, measuring the amount of an analyte in a biological sample may not give the repeatability that one would like. Small sample volumes produce reduced response from the reactions and diluting the sample with liquid reagents magnifies the problem. The present inventors have found that such problems can be overcome, making significant improvements in the accuracy and repeatability of results. In particular, it was found that improved results could be obtained by dispensing droplets in timed amounts and patterns.

SUMMARY OF THE INVENTION

The invention, in one aspect, is an improved method of assaying for the amount of an analyte contained in a biological fluid. The method comprises dispensing of two or more fractions of a sample of a biological fluid in droplets having diameters in the range of 0.05 to 1 mm onto or adjacent to a reagent containing porous substrate. The sample fractions are dispensed during predetermined periods of time, separated by periods when no dispensing occurs. Such a procedure allows reactions between the biological fluid and the reagents to occur, to permit dispensing of other liquids, or to allow reading of the results of reactions which have occurred.

Alternatively, a biological fluid may be dispensed onto a substrate, followed by reagents dispensed in small droplets for predetermined periods of time, separated by periods when no dispensing occurs.

DESCRIPTION OF THE PREFERRED EMBODIMENTS

Definitions

The following terms used herein are defined as follows:

"Spectroscopic image" refers to a detailed view of the optical response of a reagent-containing area to a biological sample deposited on the reagent-containing area, for example using a change in color, reflectance, transmission or absorbance or others such as Raman, fluorescence, chemiluminescence, phosphorescence, or electrochemical independence spectroscopy which enables examination of sub-units of the entire reagent-containing area. The image can be multi-dimensional with position (i.e. x-y) being added to the optical response.

"Hydrophilic" surfaces are those that have a less than 90° contact angle between the surface and a drop of water placed thereon.

"Hydrophobic" surfaces are those that have a 90° or larger contact angle between the surface and a drop of water placed thereon.

"Figure of Merit (FOM)" is a calculated measure of performance in which the mean difference between results obtained from samples with and without an analyte present is divided by the square root of the sum of the squares of standard deviations, the results comparing samples without the analyte and samples containing the lowest analyte concentration that can be detected.

"Coefficient of Variation (CV)" is a measure of the dispersion of a probability distribution, calculated as the ratio of the standard deviation of a set of data divided by the mean of the data.

Interaction of Liquids with Porous Substrate

The present invention provides improved control of reactions occurring on the surface and within porous substrates ("pads"), which contain dried reagents. The reactions result from the interaction between a sample liquid and a reagent-containing pad.

When a liquid sample containing an unknown amount of an analyte contacts a reagent-containing pad, the liquid must dissolve the reagent so that the reaction with the analyte can occur, which produces a detectable result e.g. a distinctive optical signal such as color, which is detected by spectrographic means. The speed at which the reaction occurs and the extent to which the result is detectable is affected by a number of factors. Such factors include the accessibility of the reagent, its solubility in the liquid, and the relative amounts of the reagent and the liquid in the region in which the liquid is placed. For example, a single drop of liquid may be effective if it is confined to a small area so that it can dissolve the necessary amount of reagent and achieve a detectable result. However, if the drop spreads over a large area the reagent may not be efficiently dissolved and the reaction may not produce a detectable result. Thus, uniform and adequate deposition of liquids on a porous pad is important if consistent and accurate results are to be obtained. Likewise, the characteristics of the pad, e.g. its hydrophobicity/hydrophilicity, its porosity and capillarity, and its thickness are also factors which determine the assay's results. In practice, one skilled in the art finds that the physical characteristics of the pad itself, the reagents, and the sample liquid all must be considered in designing a useful assay system.

In the present invention, the timed application of sample liquids, and other liquids if used, provide improved control of the interaction of the liquids with the reagent-containing pad to provide increased accuracy and uniformity of results.

Depositing Liquid Samples

In many assays, reagents are placed in porous substrates or "pads" and the substrates in strip form are dipped into the biological fluid being tested. Although such assays are useful, they are not necessarily as accurate or repeatable as desired. It was previously shown that depositing large sample droplets (i.e. 17 μL to 20.4 μL) was not as satisfactory as dipping strips in liquid. However, small droplets (i.e. 50 pL to 1 μL) provided superior results in an array of biological assays.

Two types of dispensing nozzles have been previously described. In the first, a single nozzle is used to dispense a sequence of single droplets onto the reagent-containing substrate. Either the nozzle or the substrate would be moved to provide uniform coverage in the desired area. The second type of nozzle used a plate drilled with a series of holes so that multiple sequences of droplets could be dispensed at one time. In either type, the smallest droplet size was considered to about 50 pL, which would be associated with hole diameters of about 45-50 μm. The nozzles could be operated by pressure from various sources. Using piezo actuators was one preferred method of dispensing the small droplets, which can dispense droplets at rates up to 150,000 drops per second.

Dispensing Problems

Despite the improved performance of assays in which samples of biological fluids were dispensed in small droplets, it was found that the reaction between the sample liquid and the reagents on the pad often produced a less intense result, when compared with dipping of the pad in the sample. This could be overcome by depositing greater amounts of the sample, but that required longer dispensing time and used a greater area. Since the objective of this method was to obtain better results while using less reagents in shorter times, an improved method was sought.

In addition, supplying a biological fluid as a series of small droplets was found to affect the reaction kinetics in some types of assays. That is, access of the liquid to the reagents was adversely affected, so that the period of time after dispensing the sample before the results could be read was increased.

It was found that dispensing small sample droplets in groups, separated by intervals when no droplets were dispensed, increased the development of an optical response, e.g. color, resulting from the reactions of the analyte in the sample liquid and the reagents in the porous substrate. This method is shown in the following example.

EXAMPLE 1

An assay for hemoglobin was carried out using a reagent capable of measuring peroxidatively active substances, as described in U.S. Pat. No. 5,318,894, deposited on cellulose filter paper as the substrate. A sample of urine or phosphate buffer containing 0.045 mg/dL hemoglobin was deposited from a capillary piezo dispenser in sets of 500 100 pL droplets at a rate of 85,000 drops per second and separated by short intervals of 0.75 to 3 sec. The color developed was measured by a CCD camera, was read by appropriate software and is reported as reflectance (R). Lower values of reflectance indicate greater color development. The results are requested in the following table.

| No. of droplets | Sets | Interval (sec) | Ave color @660 nm (R) | Std. Dev. (R) | % CV |
|---|---|---|---|---|---|
| 2000 | 1 | 0 | 0.66 | 0.02 | 3.6 |
| 500 | 4 | 0.75 | 0.48 | 0.02 | 4.4 |
| 500 | 4 | 3 | 0.44 | 0.04 | 7.8 |

One can conclude that dispensing the same number of sample droplets, but in a series of sets of droplets and separated by short intervals with no dispensing, provides increased color development, i.e. lower R values, and therefore more accurate results. This method is particularly useful where the analyte concentration is low and must be amplified by the detection method. In this case, the indicator or signal generating reagents are water-insoluble tetramethylbenzidine and the analyte is detected in mM amounts after catalytic reaction with other ingredients. Also, it was generally found that using a multi-hole piezo dispenser gave better results than using a single nozzle dispenser.

When a sample liquid is dispensed in a series of droplet sets, it becomes possible to make readings of the reagent-analyte reaction during the intervals when dispensing has paused. Doing so provides an opportunity to optimize the readings. As shown in the following example, added readings can improve the accuracy of the results, particularly when the amount of the analyte in the sample fluid is low.

EXAMPLE 2

An assay for protein in phosphate buffer or urine was carried out using the reagent described in U.S. Pat. No. 5,424, 215 and deposited on a glass, cellulose, polymer substrate. A sample of phosphate or urine containing from 0-1000 mg/dL albumin as the protein was deposited from a capillary piezo dispenser in sets of 500 droplets of 100 pL at a rate of 60,000 drops per second and separated by intervals of 15-120 seconds. The sample fluid contained five protein concentrations ranging from 0-10 mg/dL to 300-1000 mg/dL of protein. The results are shown in the following table, in which a Figure of Merit (FOM) was calculated for each reading period from measurements made by using a CCD camera and interpreted by appropriate software.

FOM

| Reading Interval, sec | Protein Concentration, mg/dL | | | | |
|---|---|---|---|---|---|
| | 0-10 | 10-30 | 30-100 | 100-300 | 300-1000 |
| 15 | 3.85 | 9.44 | 6.98 | 5.23 | 11.00 |
| 60 | 17.49 | 17.49 | 14.33 | 5.96 | 12.57 |
| 90 | 20.67 | 18.02 | 14.96 | 3.87 | 10.11 |
| 120 | 20.20 | 12.77 | 12.83 | 2.03 | 8.40 |

The FOM values indicate the relative accuracy of the results at the analyte (protein) concentrations tested. Higher FOM values are more desirable. One can conclude from these data that when the concentration of the analyte is low to medium a longer interval between dispensing periods provides more accurate results. However, when the analyte concentration is high, extending the interval between dispensing periods has less effect and shorter intervals are satisfactory.

In commonly assigned patent application US 2006/0263902 A1 it was shown that in a urinalysis for glucose content the Figure of Merit was improved when a urine sample was followed by dispensing of an equal volume of a pH 6.5 phosphate buffer. The improvement was believed to be related to the dilution of the sample since the chloride content inhibited the reaction of the glucose reagent. This result was further examined in the experiments reported in the following example.

EXAMPLE 3

An assay for glucose in urine was carried out using the reagent as described in U.S. Pat. No. 3,814,668 deposited on cellulose paper. Samples of urine containing 0-2000 mg/dL of glucose were dispensed as 250 droplets (50 pL) alone or accompanied by 50 pL droplets of water at a rate of 85,000 drops per second. The results were measured by using a CCD camera and read by appropriate software. They are shown in the following table.

Color Values

| | Glucose Conc., mg/dL | | | | | |
|---|---|---|---|---|---|---|
| Sample | 0 | 100 | 250 | 500 | 1000 | 2000 |
| Urine, high sp · g | 45 | 62 | 75 | 83 | 90 | 94 |
| Urine, ave sp · g | 45 | 70 | 83 | 89 | 93 | 96 |
| Urine, low sp · g | 45 | 82 | 91 | 97 | 98 | 98 |
| Water | 45 | 80 | 88 | 94 | 97 | 97 |
| 1 urine/1 water | 45 | 80 | 88 | 95 | 97 | 97 |

One can conclude from these results that dilution of the urine sample with water gave essentially the same results as were obtained with water alone as a carrier for glucose. However, the effect of specific gravity among the urine samples was large.

It was found in other experiments that dispensing the urine sample first, followed by the diluent gave better results than when the diluent was dispensed first, then the sample.

EXAMPLE 4

A dry reagent pad for protein in phosphate buffer or urine was carried out using the reagent described in U.S. Pat. No. 5,424,215 except the albumin indicator dye was omitted. A liquid dye solution was made by dissolving 3 mM of albumin indicator dye in 80% ethanol-water. The dry reagent pad sample was dipped into a urine sample containing from 0-1000 mg/dL albumin which covered the entire pad area with urine. The pad was placed into the reader and the liquid dye solution was deposited from a capillary piezo dispenser in four sets of 500 droplets of 100 pL at a rate of 60,000 drops per second and separated by intervals of 15 seconds. A second test was made with a new pad; however the dye solution was deposited from a capillary piezo dispenser in one set of 2000 droplets of 100 pL at a rate of 60,000 drops per second, without being separated by intervals when no solution was dispensed. The results are shown in the following table, in which a Figure of Merit (FOM) was calculated for each reading period from measurements made by using a CCD camera and interpreted by appropriate software.

FOM

| Reading Interval, sec | Protein Concentration, mg/dL | | | | |
|---|---|---|---|---|---|
| | 0-10 | 10-30 | 30-100 | 100-300 | 300-1000 |
| 15 sec separation interval | 13.2 | 16.4 | 12.3 | 7.6 | 11.9 |
| No separation interval | 7.3 | 6.4 | 9.1 | 3.0 | 6.3 |

The FOM values indicate the relative accuracy of the results at the analyte (protein) concentration tested. Higher FOM values are more desirable. One can conclude from these data that the use of the separation interval improves the data and that the sample can be placed on the pad and only the liquid reagent dispensed.

As shown in the examples, dispensing a biological sample in increments, separated by periods when the sample is not being dispensed, allows time for reaction with the reagents on the substrate surface, creating increased generation of the color or other detectable result. That is, dispensing all the biological sample at once is less effective. It can be concluded that the improved results are related to the use of very small droplets, (i.e. 0.1 to 1 mm diameter) which appear to react differently with reagent-containing substrates than do more conventional large droplets or dipping the substrate in the biological sample. This increase in signal generation is important in situations where the concentration of the analyte is low.

It also has been found that depositing small droplets confines the sample liquid on the surface of the substrate so that distinct spots can be seen, separated by unreacted areas. These are not necessarily easily visible to the naked eye, but are seen by the CCD camera used in these examples to provide a spectrographic image of the substrate surface. The unreacted areas have been found to have an unexpected advantage. They provide a reference color, which is detected by the CCD camera and makes possible a more accurate reading of the detectable result since the contrast with the unreacted areas is immediately available in the spectroscopic image.

While the type of substrate used will depend on the assay being run, it will be evident that such substrates may be used in various formats, including strips, cassettes, cards and the like. All of these formats will have a reagent-containing substrate positioned to receive a direct dispensing of small droplets (0.1 to 1 mm diameter) onto the substrate in patterns which provide optimal spectrographic image of the reacting surface.

What is claimed is:

1. In a method of assaying the amount of an analyte in a biological fluid wherein a sample of said biological fluid is dispensed from a nozzle in droplets having diameters in the range of about 0.05 to 1 mm onto or adjacent to a reagent-containing porous substrate and reading the results of a reaction between said dispensed biological fluid and said reagents, the improvement comprising:

dispensing said biological fluid sample onto said reagent-containing substrate in two or more fractions thereof, said fractions being dispensed in predetermined amounts for predetermined periods of time, said predetermined periods of time being separated by intervals during which said biological fluid sample is not dispensed and liquids other than said fractions of said biological fluid sample are dispensed.

2. The method of claim 1 wherein said intervals during which said biological sample is not dispensed are used to dispense liquid diluents.

3. The method of claim 1 wherein said intervals during which said biological sample is not dispensed is also used to read the results of the reaction between said dispensed biological fluid and said reagents.

4. The method of claim 1 wherein said two or more fractions of said biological fluid sample are three or more fractions.

5. The method of claim 1 further comprising the step of dispensing liquid diluents or reagents onto said porous substrate prior to initially dispensing said biological fluid sample.

6. The method of claim 1 wherein said intervals during which said biological sample is not dispensed is used to dispense additional reagents.

7. The method of claim 1 wherein said biological fluid is urine.

8. The method of claim 1 wherein said analyte is hemoglobin or protein or glucose.

9. A method of increasing accuracy and repeatability in assaying the amount of an analyte in a biological fluid comprising
(a) piezo dispensing a sample of said biological fluid onto a reagent-containing porous substrate in two or more fractions of said sample, said fractions being dispensed as small droplets in a predetermined amount for predetermined periods of time, said periods of time separated by intervals during which said biological fluid sample is not dispensed; and
(b) reading the results of a reaction between said dispensed biological fluid and said reagents during said intervals in which said biological sample is not dispensed.

10. The method of claim 9 wherein said intervals during which said biological sample is not dispensed are used to dispense liquids other than said fractions of said biological fluid sample.

11. The method of claim 10 wherein said intervals during which said biological sample is not dispensed are used to dispense liquid diluents.

12. The method of claim 10 wherein said intervals during which said biological sample is not dispensed is used to dispense additional reagents.

13. The method of claim 9 wherein said two or more fractions of said biological fluid sample are three or more fractions.

14. The method of claim 9 further comprising the step of dispensing liquid diluents or reagents onto said porous substrate prior to step (a).

15. The method of claim 9 wherein said small droplets have diameters on the range of about 0.05 to 1 mm.

16. The method of claim 9 wherein said biological fluid is urine.

17. The method of claim 16 wherein said analyte is hemoglobin or protein or glucose.

18. A method of increasing accuracy and repeatability in assaying the amount of an analyte in a biological fluid comprising:
(a) dispensing a sample of said biological fluid onto a porous substrate;
(b) piezo dispensing with a multi-hole piezo dispenser a reagent for reacting with said biological fluid in two or more fractions thereof onto said porous substrate, said fractions being dispensed in about 500 droplet sets for predetermined periods of time, said predetermined periods of time being separated by 3 to 120 second intervals during which said reagent is not dispensed; and
(c) reading the results of a reaction between said biological fluid and said reagent.

* * * * *